US010565897B2

(12) United States Patent
Crepp

(10) Patent No.: US 10,565,897 B2
(45) Date of Patent: Feb. 18, 2020

(54) QUANTITATIVE DIET TRACKING AND ANALYSIS SYSTEMS AND DEVICES

(71) Applicant: Mindful Projects, LLC, Granger, IN (US)

(72) Inventor: Justin Crepp, Granger, IN (US)

(73) Assignee: Mindful Projects, LLC, Granger, IN (US)

(*) Notice: Subject to any disclaimer, the term of this patent is extended or adjusted under 35 U.S.C. 154(b) by 0 days.

(21) Appl. No.: 15/899,711

(22) Filed: Feb. 20, 2018

(65) Prior Publication Data
US 2018/0240358 A1    Aug. 23, 2018

Related U.S. Application Data

(60) Provisional application No. 62/460,289, filed on Feb. 17, 2017, provisional application No. 62/460,302, filed on Feb. 17, 2017.

(51) Int. Cl.
*A63B 24/00* (2006.01)
*G09B 19/00* (2006.01)
*G09B 5/02* (2006.01)

(52) U.S. Cl.
CPC ...... *G09B 19/0092* (2013.01); *A63B 24/0062* (2013.01); *A63B 24/0075* (2013.01); *G09B 5/02* (2013.01); *A63B 2220/17* (2013.01); *A63B 2220/40* (2013.01); *A63B 2220/836* (2013.01); *A63B 2225/50* (2013.01); *A63B 2230/062* (2013.01); *A63B 2230/203* (2013.01); *A63B 2230/206* (2013.01)

(58) Field of Classification Search
None
See application file for complete search history.

(56) References Cited

U.S. PATENT DOCUMENTS

| | | | |
|---|---|---|---|
| 5,178,155 | A | 1/1993 | Mault |
| 5,650,945 | A | 7/1997 | Kita |
| 5,807,267 | A | 9/1998 | Bryars et al. |
| 6,468,222 | B1 | 10/2002 | Mault et al. |
| 6,554,776 | B1 | 4/2003 | Snow et al. |
| 6,572,561 | B2 | 6/2003 | Mault |
| 7,344,497 | B2 | 3/2008 | Kline |
| 7,396,331 | B2 | 7/2008 | Mack et al. |

(Continued)

FOREIGN PATENT DOCUMENTS

| | | |
|---|---|---|
| WO | 2000072754 | 12/2000 |
| WO | 2010143027 | 12/2010 |

(Continued)

*Primary Examiner* — Bruk A Gebremichael
(74) *Attorney, Agent, or Firm* — Richards Patent Law P.C.

(57) ABSTRACT

The present disclosure provides a system that quantitatively tracks an individual's diet and exercise using smart devices (phones, watches, and other wearables). Unlike existing programs, which work in energy units (calories), the present system works in mass units (grams) and satisfies the fundamental physics law of conservation of mass. Food ingested is tracked as well as exercise in order to place the user on a quantitative, custom diet that safely and effectively results in weight loss. In addition to rigorously treating the problem of weight loss by addressing the physics that underlies diet and exercise, the system empirically learns about the user over time such that performance may be optimized.

8 Claims, 12 Drawing Sheets

(56) References Cited

U.S. PATENT DOCUMENTS

| | | |
|---|---|---|
| 7,467,012 B1 | 12/2008 | Park et al. |
| 9,536,449 B2 | 1/2017 | Connor |
| 2006/0063980 A1 | 3/2006 | Hwang et al. |
| 2010/0049004 A1* | 2/2010 | Edman .................. A61B 5/1118 600/300 |
| 2011/0288381 A1* | 11/2011 | Bartholomew ........ A61B 5/024 600/301 |
| 2014/0214446 A1* | 7/2014 | Nusbaum ................ G09B 19/00 705/2 |
| 2014/0222943 A1* | 8/2014 | Oleson .................... H04L 69/16 709/208 |
| 2015/0148625 A1 | 5/2015 | Benaron |
| 2016/0004224 A1 | 1/2016 | Pi |
| 2016/0066894 A1 | 3/2016 | Barton-Sweeney |

FOREIGN PATENT DOCUMENTS

| | | |
|---|---|---|
| WO | 2011149922 | 12/2011 |
| WO | 2012085753 | 6/2012 |

\* cited by examiner

Model Inputs

| Date [Days] | Carbs [g] | Protein [g] | Fat [g] | Other Nutrients | | Exercise [steps] | Time Stamp | Weight [lbs.] |
|---|---|---|---|---|---|---|---|---|
| 41236 | 196.0 | 48.3 | 29.9 | ..... | ..... | 4419 | ..... | 121.6 |
| 41237 | 172.5 | 52.5 | 41.2 | ..... | ..... | 2880 | ..... | 121.2 |
| 41238 | 176.9 | 41.0 | 47.5 | ..... | ..... | 5323 | ..... | 121.4 |
| 41239 | 171.0 | 37.9 | 39.3 | ..... | ..... | 5435 | ..... | 120.6 |
| 41240 | 242.4 | 53.4 | 70.2 | ..... | ..... | 6510 | ..... | 121.6 |
| 41241 | 217.5 | 59.9 | 48.5 | ..... | ..... | 8111 | ..... | 121.8 |
| 41242 | 208.1 | 37.9 | 43.0 | ..... | ..... | 5407 | ..... | 121.8 |
| 41243 | 174.0 | 55.9 | 29.6 | ..... | ..... | 3391 | ..... | 121.2 |
| 41244 | 171.2 | 47.6 | 31.2 | ..... | ..... | 5446 | ..... | 121.0 |
| 41245 | 162.5 | 42.1 | 19.2 | ..... | ..... | 5112 | ..... | 120.6 |
| 41246 | 138.4 | 47.5 | 18.1 | ..... | ..... | 7893 | ..... | 122.0 |
| 41247 | 173.0 | 52.8 | 37.1 | ..... | ..... | 9008 | ..... | 121.4 |
| 41248 | 110.8 | 31.4 | 24.6 | ..... | ..... | 6074 | ..... | 120.8 |
| 41249 | 178.8 | 58.5 | 57.2 | ..... | ..... | 6053 | ..... | 121.2 |
| 41250 | 157.8 | 41.5 | 50.5 | ..... | ..... | 6762 | ..... | 121.2 |
| 41251 | 177.4 | 41.9 | 39.4 | ..... | ..... | 5528 | ..... | 122.0 |
| 41252 | 164.4 | 70.6 | 58.3 | ..... | ..... | 5293 | ..... | 121.4 |
| 41253 | 223.9 | 49.4 | 37.0 | ..... | ..... | 5191 | ..... | 123.0 |
| 41254 | 242.4 | 52.9 | 14.6 | ..... | ..... | 8585 | ..... | 123.0 |
| 41255 | 202.4 | 47.0 | 24.2 | ..... | ..... | 8112 | ..... | 122.2 |
| 41256 | 130.7 | 34.3 | 29.1 | ..... | ..... | 7027 | ..... | 121.2 |
| 41257 | 170.1 | 37.0 | 30.1 | ..... | ..... | 8206 | ..... | 120.6 |
| 41258 | 188.3 | 49.0 | 45.7 | ..... | ..... | 6475 | ..... | 121.4 |
| 41259 | 170.5 | 64.7 | 80.6 | ..... | ..... | 5050 | ..... | 122.4 |
| 41260 | 183.9 | 45.3 | 37.8 | ..... | ..... | 6451 | ..... | 121.6 |
| 41261 | 185.6 | 32.7 | 18.6 | ..... | ..... | 5640 | ..... | 122.2 |
| 41262 | 210.1 | 47.3 | 38.9 | ..... | ..... | 4575 | ..... | 122.8 |
| 41263 | 197.0 | 26.0 | 24.9 | ..... | ..... | 7788 | ..... | 122.6 |
| 41264 | 86.2 | 20.6 | 11.7 | ..... | ..... | 6979 | ..... | 121.8 |
| 41265 | 86.2 | 20.6 | 11.7 | ..... | ..... | 6982 | ..... | 122.0 |
| 41266 | 151.6 | 64.5 | 58.2 | ..... | ..... | 5971 | ..... | 122.2 |

Rows 41236–41253: Starting Data Set
Rows 41254–41266: User Input Data

QUANTITATIVE DIET TRACKING AND ANALYSIS SYSTEMS AND DEVICES

CROSS-REFERENCE TO RELATED APPLICATIONS

This application incorporates by reference and claims the benefit of priority to U.S. Provisional Application 62/460,289 filed on Feb. 17, 2017, and U.S. Provisional Application 62/460,302 filed on Feb. 17, 2017.

BACKGROUND OF THE INVENTION

The present subject matter relates generally to personalized, quantitative diet systems that operate in mass units, rather than energy units, to control a user's weight.

The obesity epidemic has systematically begun to erode the financial stability of the American health-care system. More than two-thirds of adults are now overweight, and at least one-third are considered obese (5% are morbidly obese). Obesity is linked with increasing incidence of heart disease, diabetes, Alzheimer's, cancer and other afflictions.

Although many patients are willing to consult with a nutritionist on diet and exercise, the advice provided to these patients that they should "track calories in and calories out" is fundamentally flawed. Counting calories neglects basic physics principles because it misinterprets the first law of thermodynamics, which states that energy may neither be created nor destroyed. For example, consuming 2,000 calories of doughnuts, potato chips, beer, and candy is not equivalent to consuming 2,000 calories of healthy food. Although the energy content is the same, the body's fat storage and hormonal response is different.

By working in energy units, health care professionals assert that weight gain/loss is governed by simply subtracting the number of calories expended (or "burned") from the number of calories that are ingested. This approach, which for generations has failed to produce consistent results, is flawed in at least four ways: (1) it neglects basic chemistry by ignoring the type of nutrients consumed; (2) it implicitly assumes that diet and exercise are independent variables; (3) it assumes that diet and exercise govern energy storage in the form of fat reserves, and not the other way around: in practice, hormones govern fat storage, which in turn influences diet and exercise; and (4) it ignores changes in basal metabolic rate over time.

The deeply-rooted and ingrained philosophy of working in energy units by tracking "calories in and calories out" pervades modern health care research. Worse yet, patients are often blamed for being lazy or lacking volition. Some are even convinced to undergo surgery such as liposuction, by-pass surgery, or the installation of a lap band. The reason why popular diets and fads do not work in the long run, and why so many patients fail to lose weight, is that balancing energy in-take with energy output (activity level) neglects the complex network of chemical reactions that govern the fat storage and fat dissociation mechanisms.

Conventionally, smart watches and other health tracking technologies have become popular in an effort to promote more active lifestyles. Most devices use accelerometers to track the number of "steps" recorded throughout the day or during a given exercise regimen. The results are then converted into calories that have been "burned." However, accelerometer data does not lend itself to easy interpretation of expenditure when a user is biking, lifting weights, rowing, doing push-ups, doing sit-ups, shoveling snow, or performing any of the multitude of other activities that individuals may perform throughout a given day. Accelerometers are also known to produce false-positive signals, e.g. when the user experiences a bumpy commute to work or cuts the grass with a riding lawn mower that vibrates.

Accordingly, there is a need for a system that: (1) reliably tracks all forms of exercise irrespective of the type of activity; and (2) generates a customized diet plan for an individual based on personalized data from the user, thereby overcoming the disadvantages of conventional systems.

BRIEF SUMMARY OF THE INVENTION

The present disclosure provides a system that quantitatively tracks an individual's diet and exercise using readily available smart devices (phones, watches, and other wearables). Unlike conventional programs, which work in energy units (calories), the present system uses mass units (grams) and satisfies the fundamental physics law of conservation of mass. This approach provides substantial improvement over conventional algorithms, which track "calories in and calories out," as these programs misinterpret the first law of thermodynamics.

In the present system, food ingested is tracked and, for the first time, all forms of exercise are placed on the same linear scale. The resulting program places the user on a quantitative, custom diet that safely and effectively results in weight loss (or maintenance). In addition to rigorously treating the problem of weight loss by addressing the actual physics that underlies diet and exercise, the system empirically learns about the user over time such that performance may be optimized. The system may be implemented independent of the specifics of a given smart device platform. Various examples of the systems are provided herein.

Conventional wisdom suggests that fat is somehow "burned" through a thermodynamic process while during exercise. This concept is not consistent with the fundamental physical law of conservation of mass, which states that matter cannot be created nor destroyed. In order to lose weight, fat molecules must first be dissociated into carbon dioxide and water before physically exiting the body. Following the series of chemical reactions that occur when fat molecules are liberated into their chemical constituents, the primary by-product of the fat dissociation process is carbon dioxide, which is ultimately exhaled through breath. When someone loses weight, mass is physically lost to the environment through the act of breathing (minute ventilation). For example, a person will always weigh more before going to sleep at night compared to when they wake up, just prior to "breaking the fast."

Carbon dioxide is the primary by-product of the fat dissociation process (representing 84% by mass) and is released from the body through the lungs when breathing. At the same time, breathing is inextricably tied to heart rate, and heart rate is a parameter that can be measured using readily available smart devices, such as watches, phones, or other wearables. Instead of converting steps to calories, the system can use heart rate data to estimate fat loss through carbon dioxide exhalation. This more robust approach can handle any variety of physical activities, e.g. doing the dishes, folding laundry, or writing an email, and therefore need not interpret accelerometer data waveforms nor query the user to input the type of exercise they are doing. Further, the system can track mass loss when sleeping and during less active periods while awake.

The present subject matter provides systems and methods for tracking the mass of carbon dioxide loss using the volume of air released by an individual over time. As a user exercises, the user's heart rate increases to facilitate the circulation of oxygen and other nutrients throughout the body in order to satisfy energy demands for mechanical motion. Concomitantly, as the result of exercise, ventilation through the lungs increases to continually furnish the supply of oxygen being used as fuel. Consequently, ventilation and heart rate are tightly correlated through the synchronous requirements involved in physical activity. Smart watches and other devices reliably measure a user's pulse, making it possible to connect heart rate data to the volume of air exhaled through breathing and, thereby, trace the amount of carbon dioxide released to the environment.

In an embodiment, the present system generates a dietary plan including carbohydrate mass value units, protein mass units, fat mass units, sugar mass units, fiber mass units, water mass units, among other consumed micronutrients. The system includes a controller; a memory coupled to the controller, wherein the memory is configured to store program instructions executable by the controller; wherein in response to executing the program instructions, the controller is configured to: receive a present weight value and a goal weight value from a user; receive dietary data and exercise data; generate at least two macronutrient values (for each macronutrient) based on the received dietary data, exercise data, weight data and the goal weight, wherein a first macronutrient value corresponds with a maximum amount of macronutrients the user can consume in order to achieve the goal weight in a first time length, wherein a second macronutrient value corresponds with a maximum amount of macronutrients the user can consume in order to achieve the goal weight in a second time length, wherein the first time length is greater than the second time length; and display the generated macronutrient values (for each macronutrient) on a user interface.

An advantage of the present subject matter is that it can be used to provide quantitative advice regarding the suggested consumption of sugar, protein, carbohydrates, fiber, water, and fat to reach the user's weight goals. The advice may further be combined and incorporated into helpful indices for the user to view such as glycemic index, glycemic load, insulin score, insulin load, insulin index, and other relevant tracers.

An advantage of the present system is that it can implicitly capture basal metabolic rate.

An advantage of the present system is that, unlike programs that work in energy units (counting calories), the present system operates in mass units, abiding by the law of conservation of mass.

A further advantage of the present system is that it solves problems associated with accelerometer data (such as that commonly available from smart watches and other devices that monitor heart rate) to calculate the amount of fat lost when exercising or doing any general activity, by instead tracking the amount of carbon dioxide exhaled over time by a user. Because carbon dioxide is the dominant mechanism for losing weight through the dissociation of fat molecules it may, therefore, be used to effectively track weight loss in any arbitrary circumstance involving either rhythmic or non-rhythmic motions, irrespective of exercise exertion level or type including, e.g., sitting at a desk, watching TV, or sleeping.

As described above, carbon dioxide exhalation is the dominant mechanism of weight loss, yet is not tracked by existing fitness algorithms. Smart devices in communication with the system that monitor heart rate may be used to estimate ventilation, which in turn can be correlated with the amount of carbon dioxide that exits the body when breathing. By tracking carbon dioxide exhalation over time by tracking heart rate over time, the present system can inform a user of their mass loss as a function of time. An advantage of the present system is that it does not depend on the type of activity being performed and, therefore, offers significant advantages over the use of accelerometers and other ad-hoc methods. The system may also be incorporated into programs involving diet and exercise, thereby helping users to control their weight.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIG. 2 is an example of a data set showing model inputs.

DETAILED DESCRIPTION OF THE INVENTION

The disclosure provides systems and methods, working in mass units, rather than energy units, to develop a dietary program that abides by the law of conservation of mass based on the fat storage and dissociation mechanisms of the human body. User exercise can be tracked based on one or more data platforms available from smart devices, such as phones, watches, and other wearables including sensors and/or tracking functionalities. The activity data can be uploaded and/or recorded into a data set, along with dietary information and weight measurements. From the data set, the system can create a customized, quantitative dietary plan for the user by fitting the received data to determine how the user's body responds to exercise and diet, including specific macronutrients and micronutrients. The system is structured to handle both complete and sparse data sets in a self-consistent way. The system can create a carbohydrates-versus-exercise map and a more general (multi-dimensional) macronutrients-versus-exercise-map, which is queried as a look-up-table for identifying the maximum amount of macronutrients (through interpolation) that may be consumed to maintain or lose weight.

In the system, exercise may be quantified in terms of "steps," using accelerometer data, or through more rigorous routines that involve pulse and heart-rate data. The system may empirically learn about the user over time to place the user on a quantitative, custom diet to meet the user's specified weight goal. The system may use exercise data, either in real-time on the current day or as averaged from previous days, to determine the maximum amount of one or more macronutrients (i.e., carbohydrates, protein, fat, fiber, sugar, water) that may be consumed by the user to meet the user's weight goal. Further, the system may provide specific guidance to assist the user in maintaining the user's current weight, or to lose weight at any one of a plurality of graduated rates specified thereof by the user (e.g., low intensity, medium intensity, high intensity, among others).

The present system uses smart devices to track pulse or heart rate (e.g., phones, watches, and other wearables) and works in mass units instead of energy units. In some embodiments, the system uses empirical data to train artificial neural networks using data from individual users to quantify how each user's body responds to diet and exercise. In addition to quantifying the effects of specific macronutrients on the user, the analyses may further handle considerations of glycemic index, glycemic load, insulin score, insulin load, and insulin index to quantify insulin response, insulin sensitivity, and insulin resistance.

Figure 1:
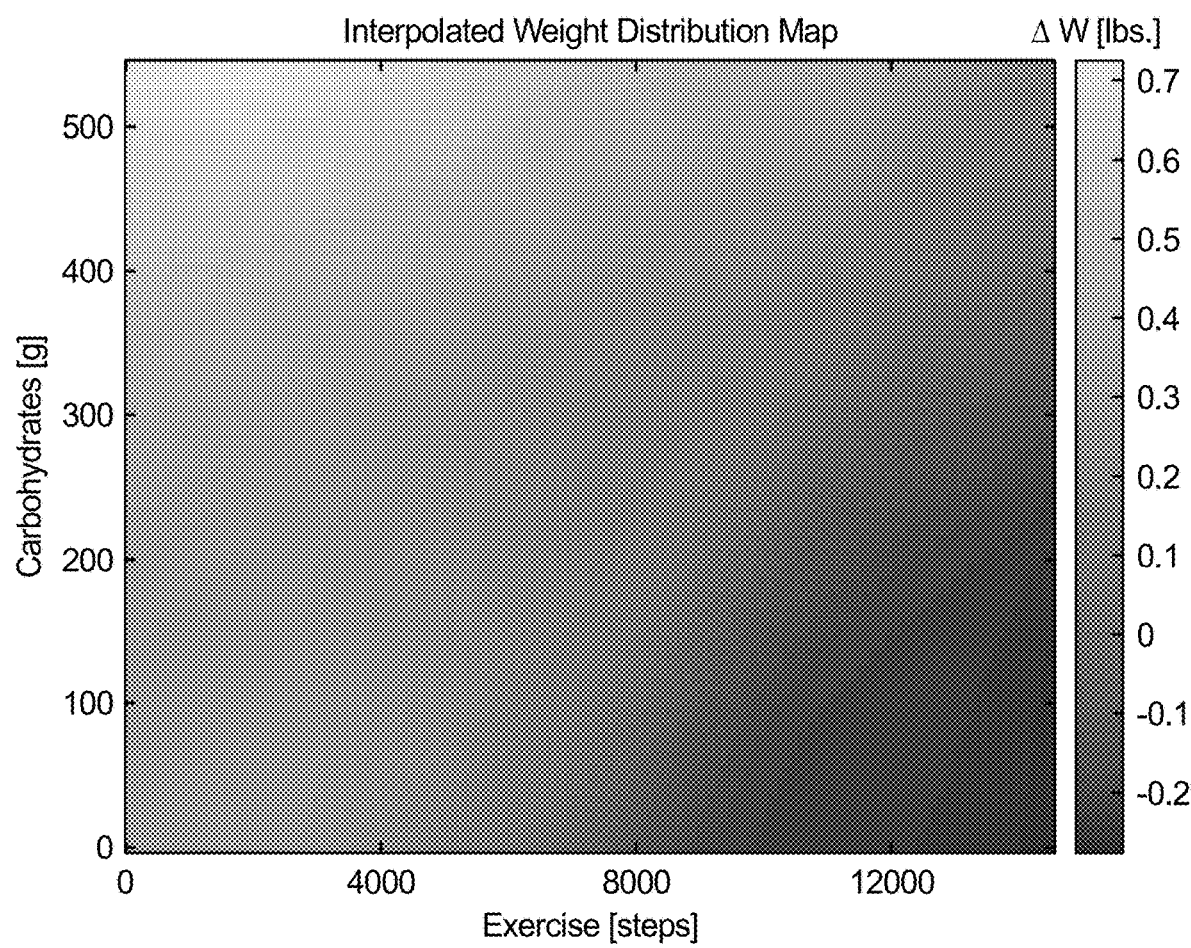
FIG. 1 is an example of a weight distribution map.

As shown in FIG. 1, the system can create a customized "map" of diet versus exercise for each user. The axis of the map corresponding to diet is quantified through macronutrients ingested in mass (e.g., grams). The other axis of the map representing exercise is quantified through "steps" taken in a given day and/or the mass of carbon-dioxide exhaled over time, and/or any other suitable metric.

In an example, as a first step, the system analyzes the historic response of a user to various levels of diet and exercise (e.g., activity level). The analysis may be based on a parametric function, a non-parametric approach, and/or one or more neural networks trained on the user's data. Subsequently, using a user interface provided through a smart device, the user identifies his or her weight goal to the system (i.e., a quantified loss, stasis, or gain). Then, based on the amount of user exercise monitored by the system, the system provides the user with a maximum amount of macronutrients the user may consume in a given time frame (e.g., week, day, meal, etc.) to meet the user's weight loss goal. The maximum macronutrient numbers are updated regularly in real-time on an ongoing basis as the currently monitored data is incorporated into the system's data set for the user. The system continues to learn about the user's response to various levels of diet and exercise and improves the accuracy of the model for the user over time.

In the system, activity levels can be tracked using readily available smart devices that employ accelerometers and/or heart rate monitors. Based on the user's activity level, the multi-dimensional macronutrients-versus-exercise map is used to calculate the maximum (or in some cases minimum) amount of carbohydrates, sugar, fat, fiber, water, and protein that may be consumed to either maintain weight or gradually lose weight in the form of fat. While the total number of calories is monitored, it is not severely restricted like conventional programs. As a result, users can eat until they are full, allowing the users to maintain their basal metabolic rate and maintain the diet over long periods of time.

In a primary example, users download software onto their phone, computer, and/or other smart device to perform the functions described herein. Alternatively, the software may be provided online in a non-downloadable format. Through a series of graphical user interfaces (GUIs), users can input profile information, such as weight, height, age, gender, and other relevant information. Based on body mass index (BMI) and other variables, the system assigns the user an initial macronutrients-versus-exercise map that most closely matches the user's demographic information based on the user profile data received. The initial map can be used as an initial estimate when assigning a starting point for the user's weight loss program.

The system can create maps, and subsequently customized weight goal programs, by tabulating the user's daily nutrient intake. In an example, the user's daily dietary and/or exercise input may be uploaded from an associated fitness application. In addition, the user can input food consumed, or planned to be consumed, for each meal and create meal entries through custom recipes. The user can manually enter each food item and/or select food from a menu the system provides. For example, a plurality of restaurant menu items can be provided from which a user can select. In another example, a user can upload photos of meals consumed to can be analyzed by the system for nutrient data. The system can analyze and breakdown the dietary intake into various macronutrients and micronutrients, wherein the analysis can be stored into a secure data set associated with the user.

Food items for meal consumption and/or planning (e.g., for meal planning within the weight loss goal) can be selected from listed food items on a display on the user interface from any major or minor food groups such as, though not limited to: bakery (muffins, rolls, buns, croissants), breads, beverages (alcoholic and non-alcoholic), cakes, cereals, cookies, crackers, candies, cold-cut-meads, dairy, eggs, fats, fish, fruits, grains, meats, nuts and seeds, pasta, vegetables, yogurts (including brands names, frozen yogurts and ice-creams), etc. If a food item is not depicted, the user can create a new entry into the system and the system can determine the nutritional information associated with the food item. Users can choose the size and/or amount of a food item by selecting: weight, volume, macronutrients, calories or serving size.

In addition, the user can also regularly input into the system his or her weight using a precise scale. The user may be encouraged to do so at least once per day, though other time intervals are also acceptable. Alternatively, the user's present weight can be automatically uploaded from a smart scale or any other weight tracking application directly into the system.

Any input data associated with the user and user profile can be stored along with the time stamp of the data/measurement into the database. Users that do not regularly record their diet, exercise, and weight can have "static" maps that are not fully customized. Users that consistently record their weight, activity, and/or diet data can have "dynamic" maps that become gradually more customized with time allowing the system to effectively learn about each user's body and help to more accurately customize each user's diet plan over time.

FIG. 1 shows an example of a carbohydrates-versus-exercise map created by the system. When a user consumes too much of a given macronutrient (most often sugar and carbohydrates correlate most strongly and have the highest insulin response) for a given level of exercise (top-left portion of plot), the user will generally gain weight. When a user's exercise level exceeds a certain threshold, based on the amount of carbohydrates ingested, the user will lose weight (bottom-right portion of plot). In between these regimes exist contours that correspond to weight maintenance (change in weight equals zero) whereby a user may sustain his or her current BMI by quantitatively matching macronutrient intake to exercise level.

Although carbohydrates and sugar correlate most strongly with weight gain, they may not be the only nutrients involved in the system's calculations. Protein, fat, fiber, sugar, water, and other quantities (e.g., glycemic load, glycemic index, insulin score, insulin load, insulin index, etc.) may be used in a macronutrient-versus-exercise map. For example, one or more of these macronutrients may be provided manually by the user or derived automatically from nutritional input. Such maps may be derived through statistical marginalization by randomly drawing from the user's actual distribution of nutrient intake when creating a map from the statistical algorithm (often a neural network).

FIG. 2 shows an example of a user data set. The user data set may be actual user data. However, when initializing the system, the starting data may be obtained from a library of other users by inputting values from users of comparable demographics (e.g., age, gender, BMI, etc.). Such borrowed data acts similar to a "Bayesian prior." The artificial neural network culls entries for macro and micronutrient data along with exercise level, measured in either steps or integrated heart rate (such as CO2), as input to estimate the user's weight as a function of time. As the user inputs additional information, the system learns about the individual by updating the macronutrients-versus-exercise map, thus more accurately reflecting the user's body's response to diet and exercise.

Accordingly, the system is trained using nutrients and exercise level to model and predict a user's weight as a function of time. New users download a training set that is based on their BMI, age, gender, and other relevant information. Over time, as the users enter additional data (e.g., real time diet, exercise, and weight data) the system customizes the weight projection. In other words, as personalized data is input, the system learns about the user's body's response to diet and exercise and modifies the fitness plan and weight projection accordingly.

Figure 3:
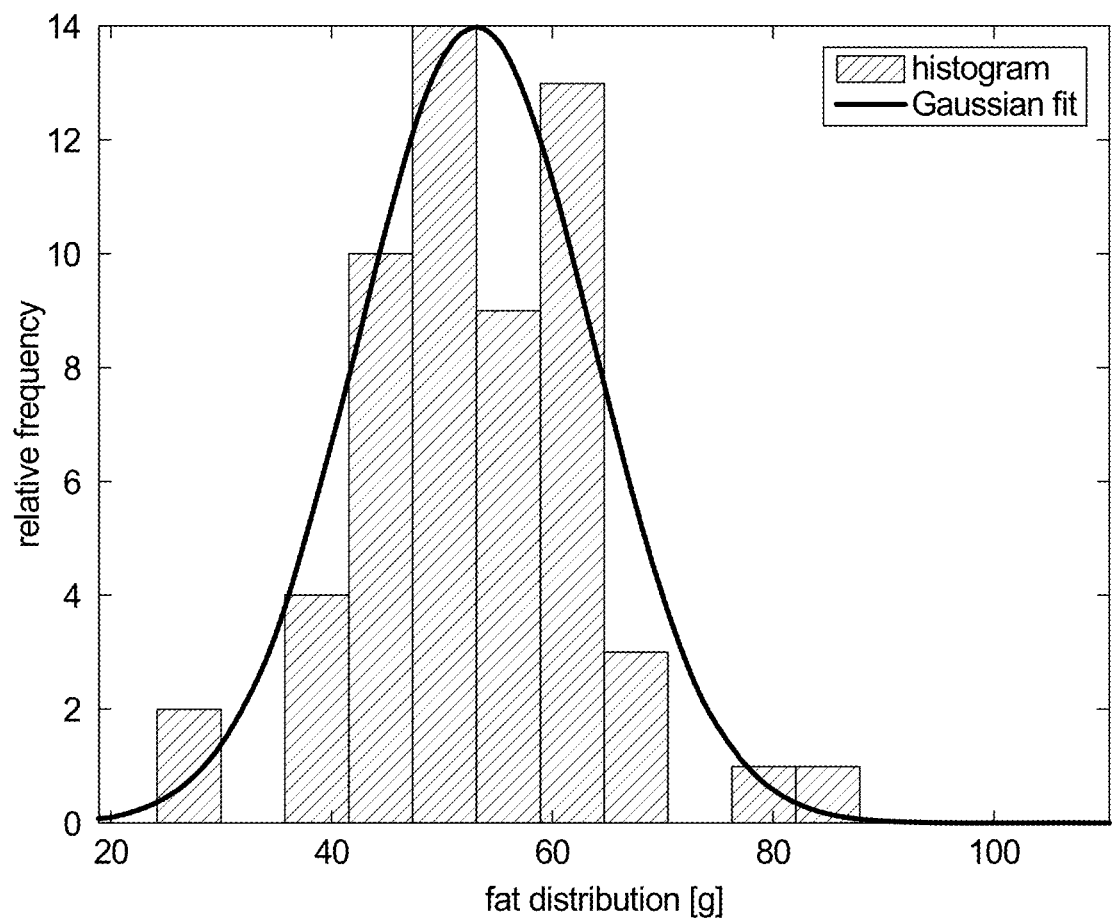
FIG. 3 is an example of a histogram data illustrating the relative number of grams of fat consumed per day for a user.

FIG. 3 is an example of histogram data showing the relative number of grams of fat consumed per day for a user. Similar distributions can be tabulated for protein, fiber, sugar, water, and other macro and micronutrients for the statistical marginalization process when training, validating, and testing a neural network, parametric model, or non-parametric model.

The system can fit user data by relating diet (macro- and micro-nutrients) and exercise (either steps or heart rate data) to patterns found in the user's weight as a function of time. For example, the system can fit user data to weight patterns of the specific user (e.g., based on the historical data of the user) and/or weight patterns of an ensemble (plurality) of users with similar demographics or profile to that of the user.

Figure 4:
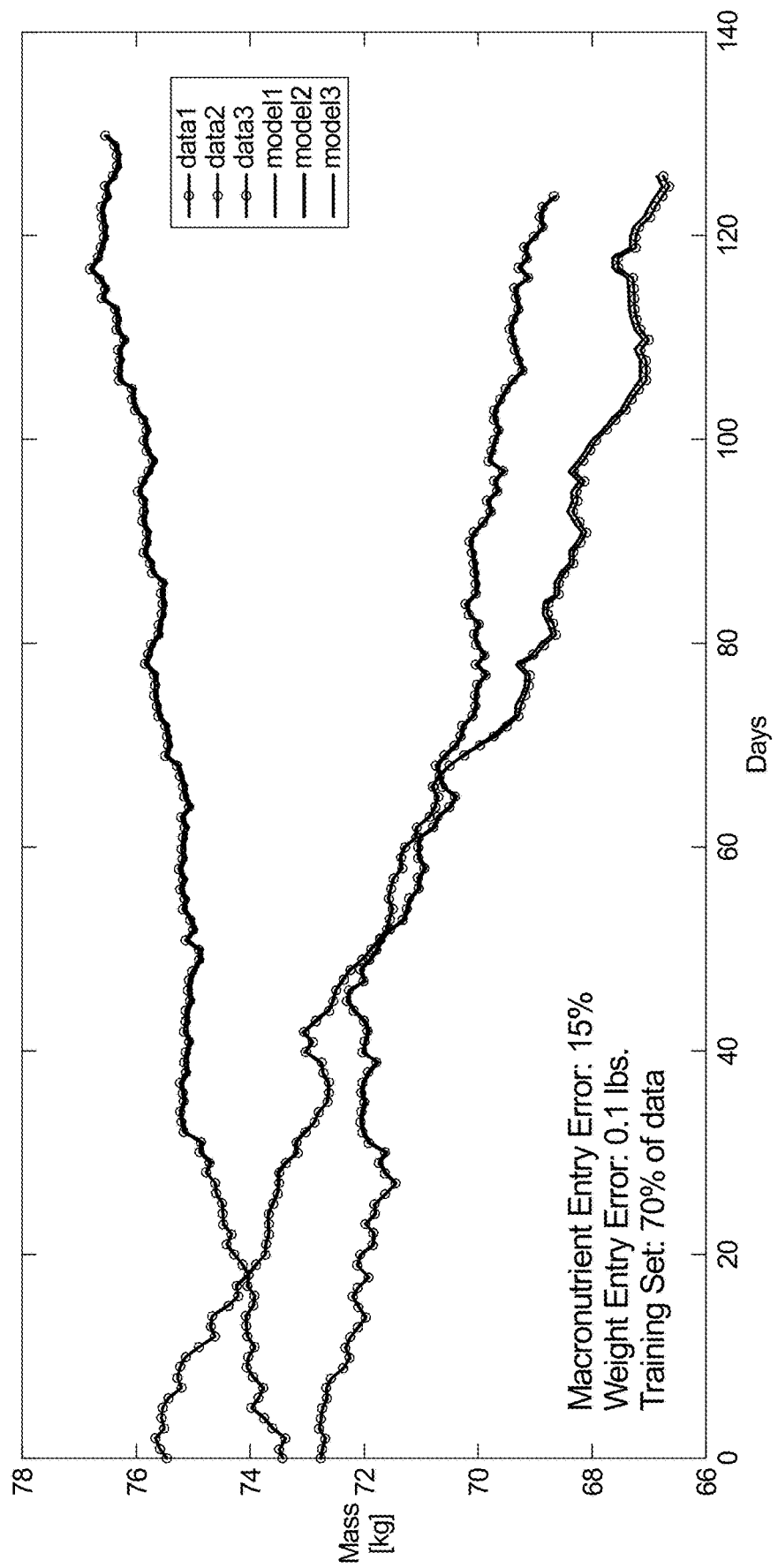
FIG. 4 is a graph of a fitting for mass versus days for three different people.

FIG. 4 illustrates an example using several different users' data sets. One or more machine-learning and other techniques including, but not limited to, Levenberg-Marquardt, least squares, Markov Chain Monte Carlo, Bayesian analysis, back-propagation, deep learning, and other routines (both static and dynamic algorithms) may be implemented to minimize residuals between the users' predicted weight, based on diet and exercise, and their actual weight. Training, validation, and testing sequences are employed to balance fit residuals against available degrees of freedom through optimization of the number of hidden layers and number of neurons involved in network calculations. Calculations may be done remotely or locally on the user's smart device or through a cloud server implementation using any variety of languages such as Octave, Matlab, Python, Java, C, C++, or other software packages.

Specifically, FIG. 4 includes an example data set for three individuals demonstrating the use of a neural network for fitting mass versus time. Macronutrient information (e.g., carbs, protein, fat, fiber, water, etc.) is recorded, as well as exercise level (e.g., steps, carbon dioxide expelled, integrated heart rate, among others) to predict the patient's weight. Each person consumes a different amount of calories per day and portions of carbohydrates, protein, fats, etc. Each body has a different inherent response to these variables. The present system can empirically track a user's progress towards the user's weight gain/loss/maintenance goals with realistic uncertainties in nutrient intake (15%) and weight errors of +/−0.1 lbs. when training the neural network. Smaller uncertainties allow for faster algorithm convergence.

The system can regularly update a user's diet-versus-exercise map (e.g., the macronutrient-versus-exercise map of FIG. 1). The system updates generally occur once per day or when the user inputs new dietary and weight information via the application. As more dietary, exercise, and weight information is provided, the statistical algorithm effectively "learns" about the individual by augmenting the user's table of input data. In other words, the system does not merely generate a weight loss or weight maintenance plan based on calories in (consumed food) versus calories out (exercise). Instead, the system analyzes the historical data from a user (i.e., the specific food consumed in combination with the user's exercise) to determine empirically how the user's body changes weight according to diet and exercise.

In one embodiment, the user's exercise level is quantified each day (or any time interval) using a smart watch, wearable, or similar device. The resulting value corresponds to a certain number of steps (or integrated heart rate) specifying a location on the exercise axis of the carbohydrates-versus-exercise map. The maximum amount of macronutrients is calculated based on the user's change in weight estimated by the system for various levels of diet and exercise. The maximum amount of macronutrients that may be consumed is most conveniently, but not necessarily, provided for the user over a 24-hour period, depending on the application settings. The maximum (and minimum) amount of macronutrients may also be continuously updated in real-time based on the user's exercise and food intake. For example, the user can input one meal at a time or an entire day or week's food consumption at once. Similarly, the user can input each exercise in at a time or a day or a week's worth of work outs at once. Meanwhile, heart-rate (and/or steps) are automatically captured by the fitness tracker or smart device. In some embodiments, the system can generate maximum macronutrient values for each day, while further breaking down the weekly and daily macronutrient values into specific meal times and snacks.

The system can modify the exercise and diet plan based on the diet and exercise data entered. For example, after entering a morning meal and exercise, the system can calculate and display the maximum number of macronutrients the user can have at lunch, dinner, and/or snacks for the remainder of the day to stay on track towards the user's weight maintenance or weight loss goals. The system can modify the next meal's, next snack's, next day's, next week's maximum carbohydrate and sugar (and/or insulin index or insulin load) consumption to reach the identified weight goals of the user. For example, the system can analyze the macronutrient content of the food consumed in previous meals and compare it to the previous meals' goals. The system can update the daily plan (e.g., the next three meals) based on the "total amount of carbohydrate and sugar consumed" of all meals preceding that exceeds the "sum of all carbohydrate and sugar goal" (e.g., the maximum carbohydrates and sugar value) to meet the weight loss or maintenance goal.

FIGS. 5A-5D illustrate examples of a graphical user interface through which the features and functions of the systems and methods described herein may be executed. Through the GUI shown, users may specify whether they wish to maintain their current weight or to lose weight (in some examples, the users may even specify weight gain desired). As shown in the graphical user interface in FIG. 5A, fiducial levels of fat loss described as, e.g., "gradual/low intensity," "moderate/medium intensity," or "aggressive/high intensity" are provided as a reference point. In addition to these discrete levels, the user may use one or more sliders (an example of a slide is shown on the right side of the vertical carbohydrate scale in FIG. 5A) to more finely specify a weight loss goal. For example, if a user selects an "aggressive" intensity for achieving his or her weight loss goal, the system can generate an exercise and diet plan for achieving the weight loss in a shorter time period than if the user selected a "gradual" or "moderate" intensity.

Exercise activity (e.g., exercise duration and/or intensity level) can be automatically incorporated into the user data set by syncing the program to devices that measure steps and/or heart-rate. Users can load their dietary and/or exercise information directly into the system and/or by interacting with fitness programs, the data from which can be integrated into the system. Body weight can be entered via the user interface and the associated time of day may be recorded by accessing the time stamp provided by the associated smart device. This data, along with diet data, can be used as parameters by the system. By interacting with the application shown in FIGS. 5A-5D, the user has access to a quantitative method for monitoring and controlling the user's weight.

Figure 5A:
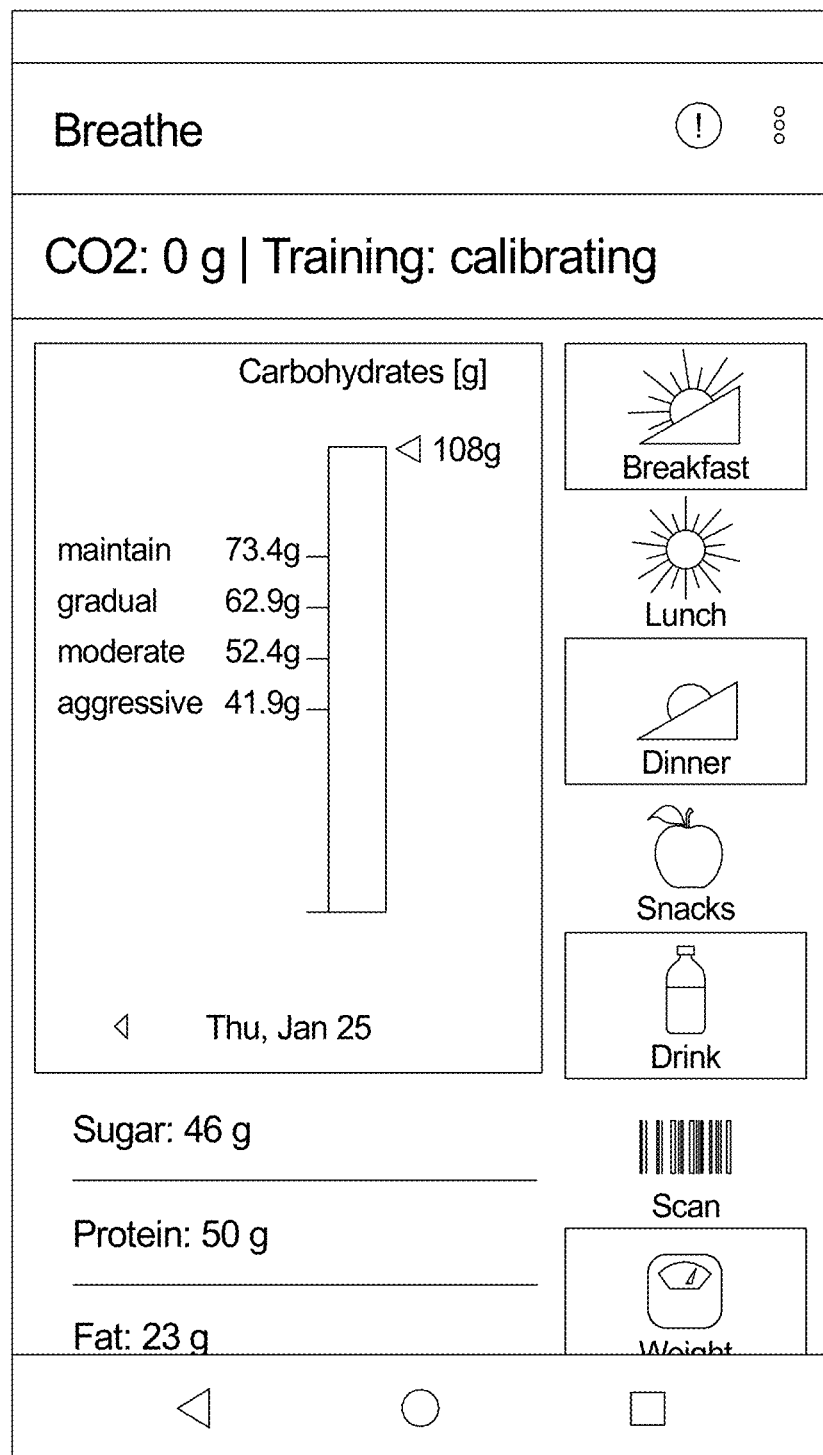
FIGS. 5A-5D are examples of a user interface illustrating various functionalities of the system.

The example shown in FIG. 5A illustrates an example of a user interface depicting carbon dioxide weight loss through exhalation along with activity level (e.g., steps, integrated heart rate, etc.). Buttons and/or prompts are provided by the system for entering a user's weight as well as connecting to various fitness applications in the smart device to automatically upload further data (e.g., activity, dietary, etc.) for the system to take into account.

Figure 5B:
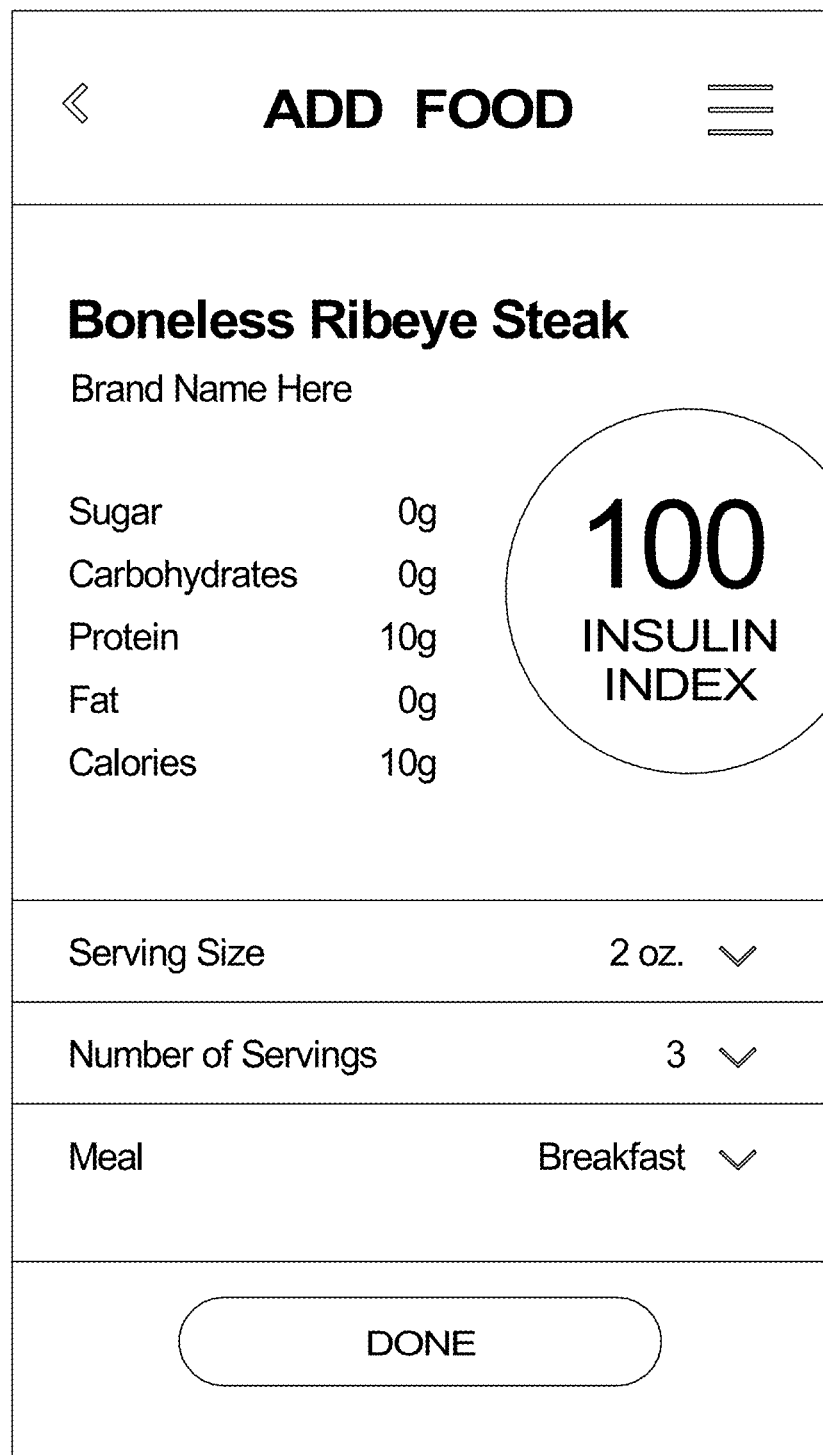
Figure 5C:
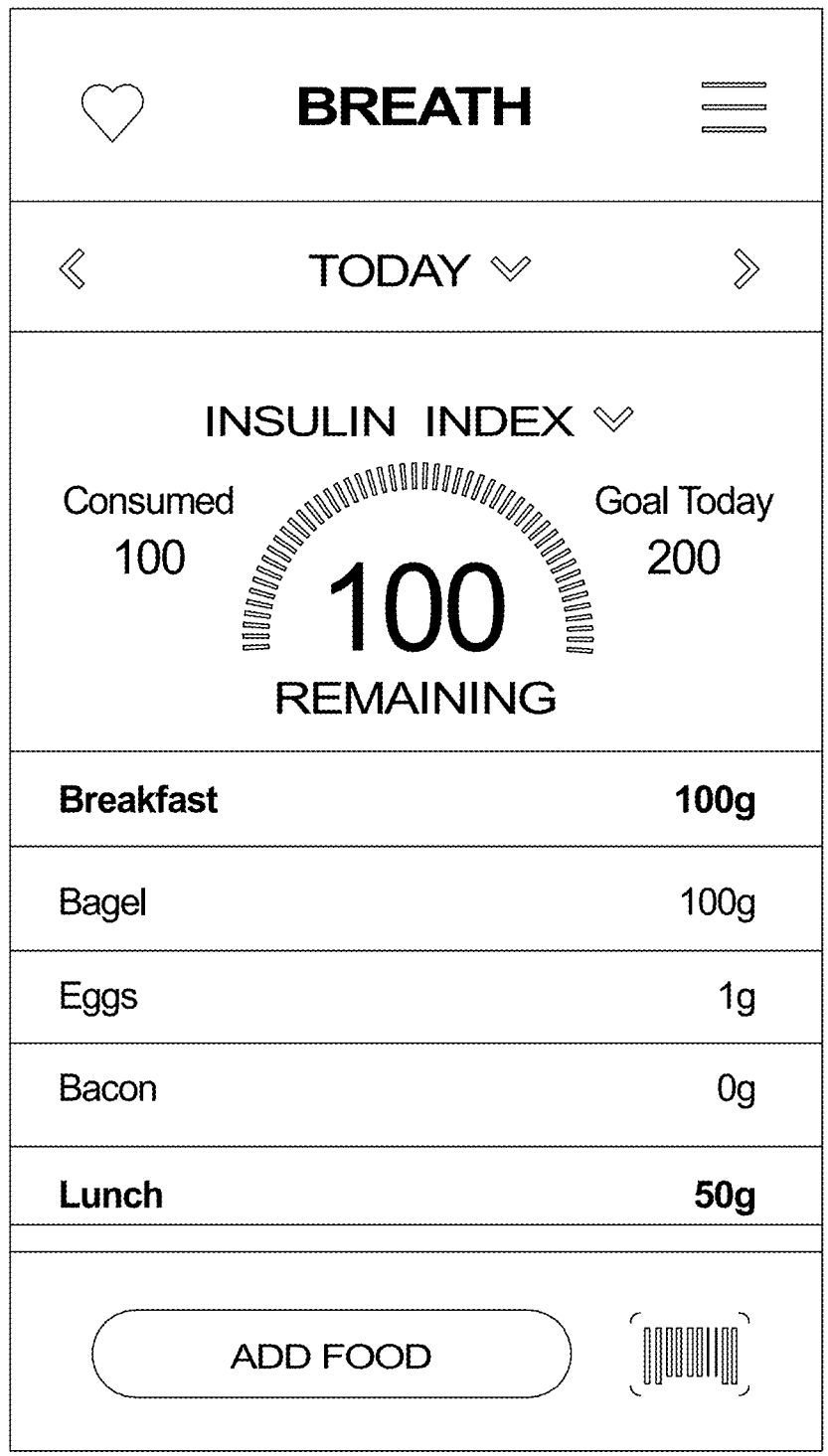
Figure 5D:
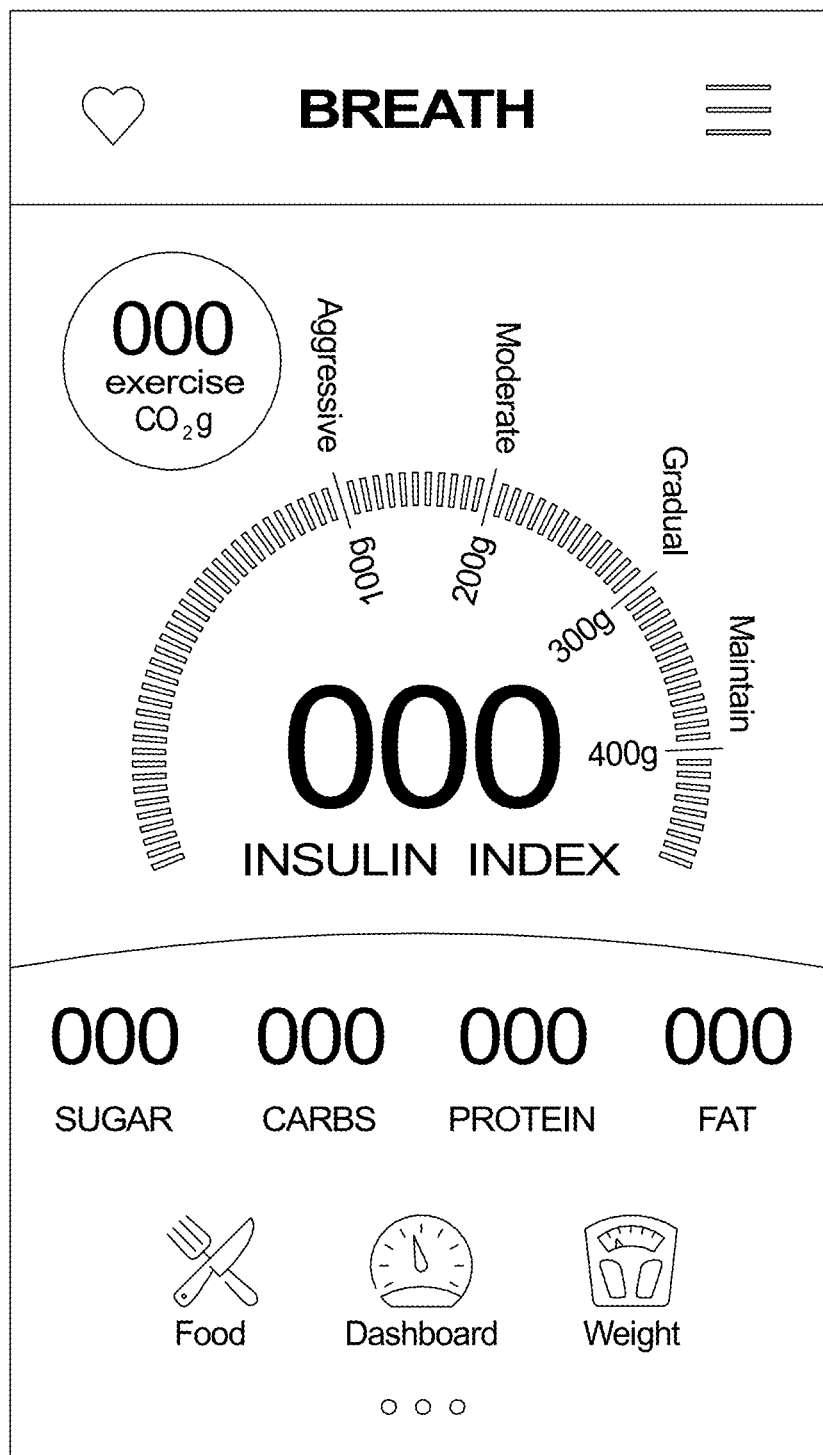

FIG. 5B illustrates a user interface depicting functionality for a user to enter consumed food, wherein the system can display the details of the consumed food. FIG. 5C includes a user interface depicting input and tracking functionality in terms of an insulin index. FIG. 5D illustrates a user interface depicting the insulin index based on varying intensity goals (e.g., maintain, gradual, moderate, and aggressive). As shown, the input data can be calculated for sugar, carbs, protein, and fats.

In embodiments of the systems and methods described herein, carbon dioxide mass loss is tracked using the volume of air released by an individual over time. As a user exercises, their heart rate increases to facilitate the circulation of oxygen and other nutrients throughout the body in order to satisfy energy demands for mechanical motion. Ventilation through the lungs concomitantly increases as the result of exercise to continually furnish the supply of oxygen being used as fuel. Consequently, ventilation and heart rate are tightly correlated through the synchronous requirements involved in physical activity. Smart watches and other devices reliably measure a user's pulse, making it possible to connect heart rate data to the volume of air exhaled through breathing and thereby trace the amount of carbon dioxide released to the environment. It is contemplated that the preferred embodiments of the systems described herein will use carbon dioxide monitoring to more accurately learn the user's body's response to activity and nutrition.

Figure 7:
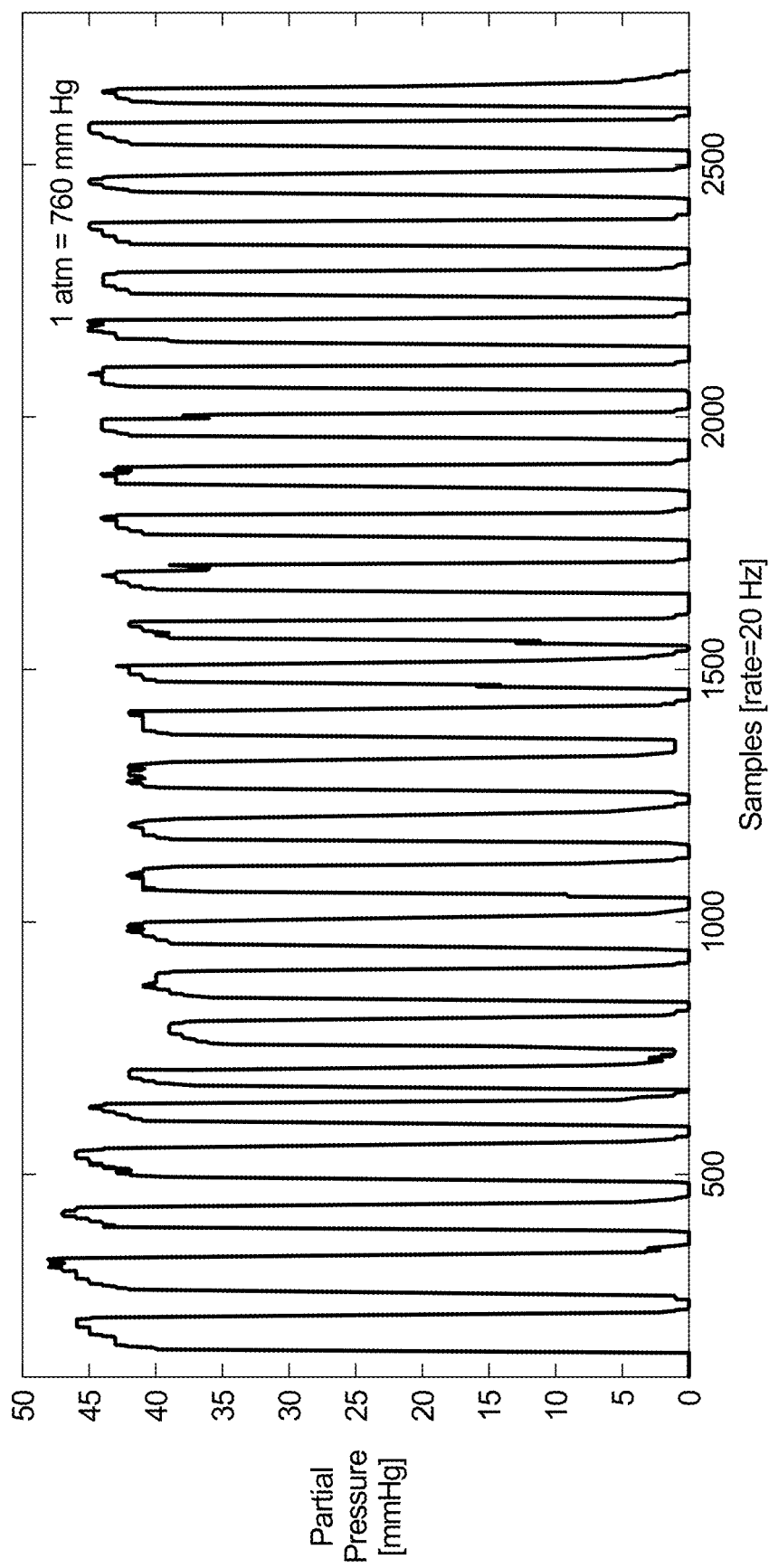
FIG. 7 is a graph of samples versus partial pressure.

"Minute" ventilation is related to heart rate (HR) by the expression $$\dot{v}=a+b\ \ln(HR)+\text{correction terms},$$

where $\dot{v}$ represents the volume of air in liters released by an individual in one minute and a and b are coefficients of the empirical fit that depend on age, gender, fitness level, and other variables. As an example, from Haines & Raizenne 1992, the entirety of which is incorporated herein by reference, typical values for a and b coefficients from a statistically significant ensemble of test subjects are approximately a=0.806 and b=0.016. Additional correction terms may be applied to reduce scatter in data fit residuals, such as including body surface area (BSA), weight, or physical work capacity (PWC) values. The fractional composition of exhaled air that is carbon dioxide is approximately 5%, as shown in FIG. 7, which displays experimental measurements of $CO_2$ fractional composition as a function of time using a direct capnography machine.

More generally, each user has different empirical coefficients that relate heart rate (HR) to ventilation and other quantities. The a, b, and other coefficients are found through calibration of the $CO_2$ algorithm by monitoring HR as a function of time when the user is fasting based on a mass loss rate that is measured using an accurate scale.

The mass of carbon dioxide exhaled per time, $m_{CO_2}$, is found by multiplying the minute ventilation by the density of air, $\rho$, taking into account the molecular weight of $CO_2$ compared to air, $$m_{CO_2}=\dot{v}_{CO_2}\rho r^{-1}$$

where r=29 g $mol^{-1}$/44 g $mol^{-1}$.

Given the mass of carbon dioxide release over time, the amount of fat physically lost to the environment is determined based on the dissociation of fat molecules. Oleate ($C_{18}H_{34}O_1$), palmitate ($C_{16}H_{32}O_2$), and linoleate ($C_{55}H_{104}O_6$) are the three most common fatty acids found in adipose tissue and all esterify to form $C_{55}H_{104}O_6$. This molecule can dissociate into carbon dioxide and water via the pathway 10 kg $C_{55}H_{104}O_6$+29 kg $O_2$→28 kg $CO_2$+11 kg $H_2O$.

Approximately 84% of fat lost to the environment is in the form of carbon dioxide with water making up the remainder (Meerman & Brown 2014, the entirety of which is incorporated herein by reference). Taking the above chemical reactions into account,

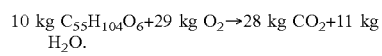

Thus, heart rate data from a smart device may be used as a proxy for the amount of $CO_2$ released to the environment from fat dissociation through ventilation working in mass units. Since heart rate increases and decreases commensurate with the intensity of a user's activity and fitness level, it serves as a convenient tracer for fat loss.

Figure 6A:
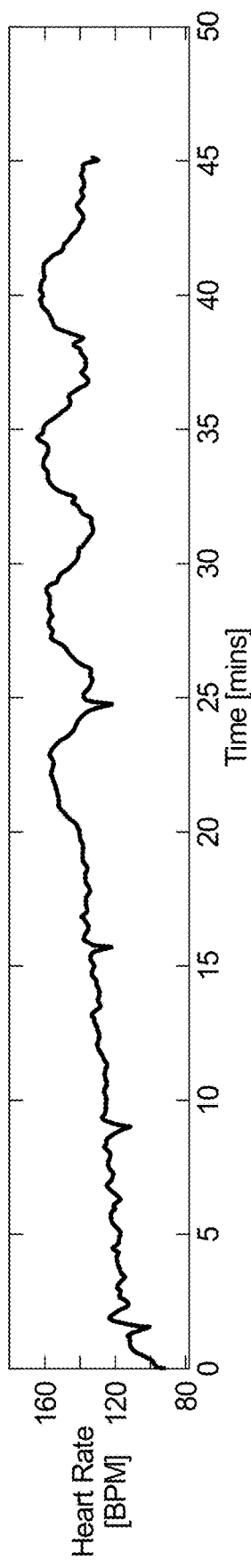
FIGS. 6A-6C is an example of heart rate, fat loss, and a cumulative summation, respectively, as a function of time in mass units.
Figure 6B:
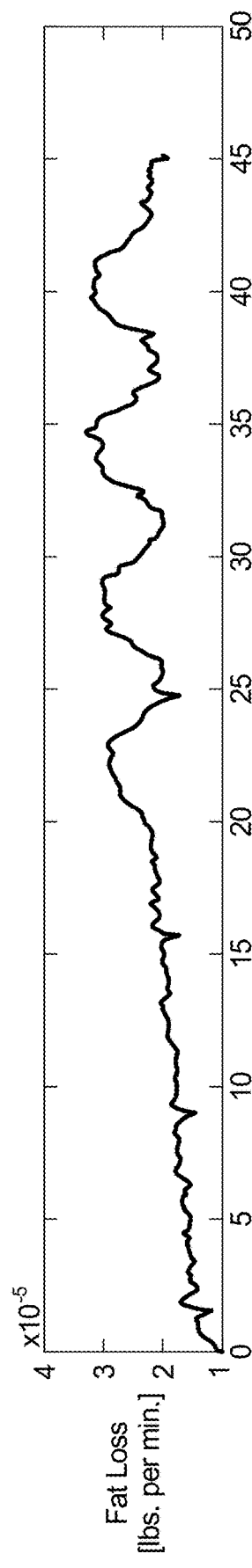
Figure 6C:
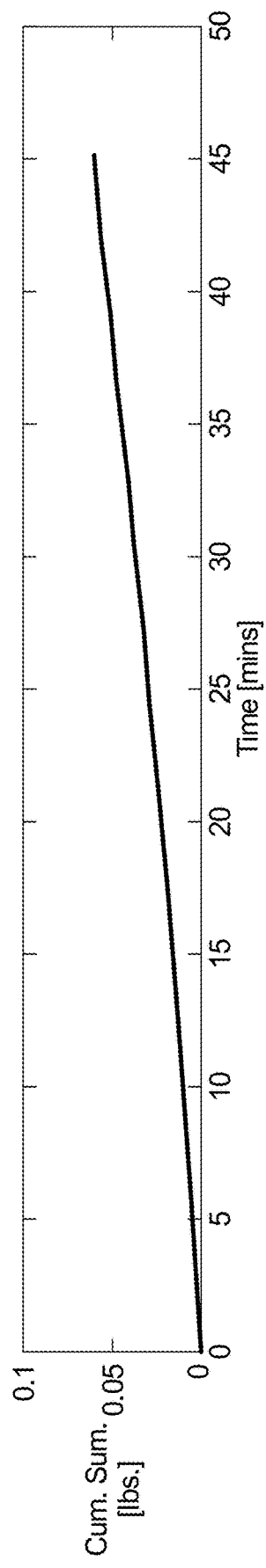

FIGS. 6A-6C illustrate an example of the algorithm when converting heart rate data to mass loss through exhalation of carbon dioxide. Uncertainty in the above relations is generally small, no worse than calorie expenditure estimators, and is limited by knowledge of the user when determining best-fit coefficients in the empirical relationship between heart rate and minute ventilation. Artificial neural networks and other statistical methods (parametric, nonparametric, etc.) may be used to incorporate input (change in) weight and dietary values from the user and to calibrate the amount of mass lost over time. The respiration exchange ratio (RER) is naturally incorporated into the analysis based on user input dietary information to calibrate the relative fraction of carbohydrates versus protein versus fat that is being predominantly used for fuel.

FIG. 6A illustrates a user's heart rate in beats per minute (BPM) that can be tracked using a smart device. In this case, a series of four high-intensity interval sessions is performed on a treadmill. FIG. 6B illustrates the amount of fat lost to the environment in units of mass-per-time that is calculated using the equations described previously herein. The nonlinear relationship between heart rate and minute ventilation makes it possible to increase significantly the amount of fat lost to the environment when exercising. FIG. 6C illustrates a cumulative summation of fat loss plotted as a function of time. An application can be installed on a smart device that can keep track of $CO_2$ and fat loss in mass units when provided with access to a user's heart rate data.

The present system can include a method for using the plurality of heart rate data and sensors from smart devices such as phones, watches, and other wearables to track carbon dioxide mass loss and fat dissociation as a function of time through the mechanism of exhalation. The sensors can include heart rate monitors, pulse data, blood pressure data, pulse oxygen level, among others. Fat dissociation can be tracked irrespective of the type or kind of exercise, even when the user is idle, sleeping, or otherwise. In addition, the system can take into account dietary programs that compare nutrient intake to exercise in an effort to control weight. The system may also take into account users from a diverse demographic in age, gender, height, weight, and other variables, by calibrating the empirical relationship between heart rate and ventilation.

As mentioned above, aspects of the systems and methods described herein are controlled by one or more controllers. The one or more controllers may be adapted to run a variety of application programs, access and store data, including accessing and storing data in the associated databases, and enable one or more interactions as described herein. Typically, the controller is implemented by one or more programmable data processing devices. The hardware elements, operating systems, and programming languages of such devices are conventional in nature, and it is presumed that those skilled in the art are adequately familiar therewith.

For example, the one or more controllers may be a PC based implementation of a control processing system utilizing a central processing unit (CPU), memory and an interconnect bus. The CPU may contain a single microprocessor, or it may contain a plurality of microprocessors for configuring the CPU as a multi-processor system including cloud implementations. The memory may include a main memory, such as a dynamic random access memory (DRAM) and cache, as well as a read only memory, such as a PROM, EPROM, FLASH-EPROM, or the like. The system may also include any form of volatile or non-volatile memory. In operation, the memory stores at least portions of instructions for execution by the CPU and data for processing in accord with the executed instructions.

The one or more controllers may also include one or more input/output interfaces for communications with one or more processing systems. Although not shown, one or more such interfaces may enable communications via a network, e.g., to enable sending and receiving instructions electronically. The communication links may be wired or wireless.

The one or more controllers may further include appropriate input/output ports for interconnection with one or more output mechanisms (e.g., monitors, printers, touchscreens, motion-sensing input devices, etc.) and one or more input mechanisms (e.g., keyboards, mice, voice, touchscreens, bioelectric devices, magnetic readers, RFID readers, barcode readers, motion-sensing input devices, etc.) serving as one or more user interfaces for the controller. For example, the one or more controllers may include a graphics subsystem to drive the output mechanism. The links of the peripherals to the system may be wired connections or use wireless communications.

Although summarized above as a PC-type implementation, those skilled in the art will recognize that the one or more controllers also encompasses systems such as host computers, servers, cloud servers, workstations, network terminals, and the like. Further one or more controllers may be embodied in a device, such as a mobile electronic device, like a smartphone or tablet computer. In fact, the use of the term controller is intended to represent a broad category of components that are well known in the art.

In each implementation, security protocols may be implemented to protect user data according to e.g. HIPAA compliance considerations.

Hence aspects of the systems and methods provided herein encompass hardware and software for controlling the relevant functions. Software may take the form of code or executable instructions for causing a controller or other programmable equipment to perform the relevant steps, where the code or instructions are carried by or otherwise embodied in a medium readable by the controller or other machine. Instructions or code for implementing such operations may be in the form of computer instruction in any form (e.g., source code, object code, interpreted code, etc.) stored in or carried by any tangible readable medium.

As used herein, terms such as computer or machine "readable medium" refer to any medium that participates in providing instructions to a processor for execution. Such a medium may take many forms. Non-volatile storage media include, for example, optical or magnetic disks, such as any of the storage devices in any computer(s). Volatile storage media include dynamic memory, such as the memory of such a computer platform. Common forms of computer-readable media therefore include for example: a floppy disk, a flexible disk, hard disk, magnetic tape, any other magnetic medium, a CD-ROM, DVD, any other optical medium, punch cards paper tape, any other physical medium with patterns of holes, a RAM, a PROM and EPROM, a FLASH-EPROM, any other memory chip or cartridge, or any other medium from which a controller can read programming code and/or data. Many of these forms of computer readable media may be involved in carrying one or more sequences of one or more instructions to a processor for execution.

Figure 8:
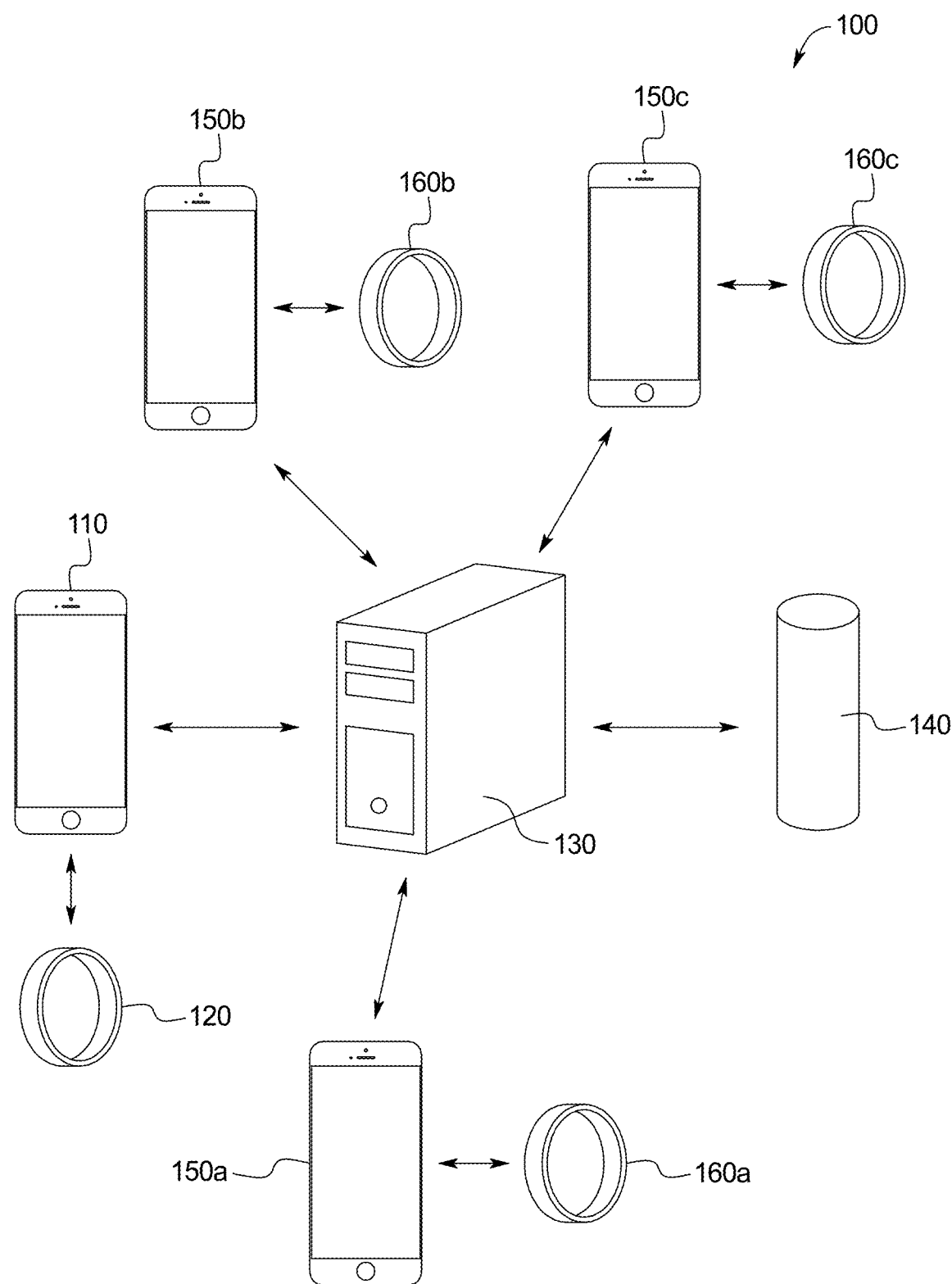
FIG. 8 is a schematic of an example of a system for generating a dietary plan including macronutrient mass value units.

FIG. 8 illustrates an example of a system 100 for generating a dietary plan including macronutrient mass value units. As shown, the system 100 includes a first user device 110 in communication with a first user fitness tracker 120. The first user device 110 is further in communication with a server 130 which communicates with a database 140. The server 130 is also in communication with a plurality of other user devices 150a, 150b, 150c, each of which is in communication with their associated other user fitness trackers 160a, 160b, 160c.

In the example shown in FIG. 8, the first user device 110 is a smartphone (shown in greater detail in FIG. 9) that operates software to present the user with a GUI such as the example GUI shown in FIGS. 5A-5D. Through the GUI, the user provides information to the system 100 and interacts with the features and functions of the system 100. For example, the user may set a weight goal, select an intensity for the user's approach to the weight goal, receive guidance regarding a maximum quantity of one or more macronutrients the user may consume over a selected time frame to meet the selected weight goal at the selected intensity, provide information regarding the user's activity and nutrition, etc.

Some, or all, of the user's activity information may be derived through communication with the first user fitness tracker 120. For example, the first user fitness tracker 120 may be a wearable device that includes both a heart rate monitor and an accelerometer through which the first user fitness tracker 120 collects data about the user's heart rate (which is used to derive the user's rate of exhalation of carbon dioxide), as well as the user's activity (e.g., the number of steps taken by the user, etc.).

The server 130 and the database 140 are the central brains of the system 100 and are in communication with each of the first user device 110 and the plurality of other user devices 150a, 150b, 150c. The server 130 includes the processor that carries out the functions of the system 100 that operate remote of the first user device 110. For example, the server 130 and the database 140 collect the user data from each of the first user device 110 and the plurality of other user devices 150a, 150b, 150c to build the data sets from which the algorithms described herein are trained. The server 130 and the database 140 may also collect and store the real-time data used to update the guidance to the users through the first user device 110 and the plurality of other user devices 150a, 150b, 150c based on what is learned from analysis of the data sets.

Importantly, one can see from the example shown in FIG. 8 that the real-time data received from one or more of the other user fitness trackers 160a, 160b, 160c and communicated to one of the other user devices 150a, 150b, 150c, which in turn is communicated to the server 130 and database 140, may be used to compute adapted guidance that can be communicated to the first user through the first user device 110. Such interconnection between each of the elements of the system 100, illustrates how robust and interconnected the system 100 can be.

Figure 9:
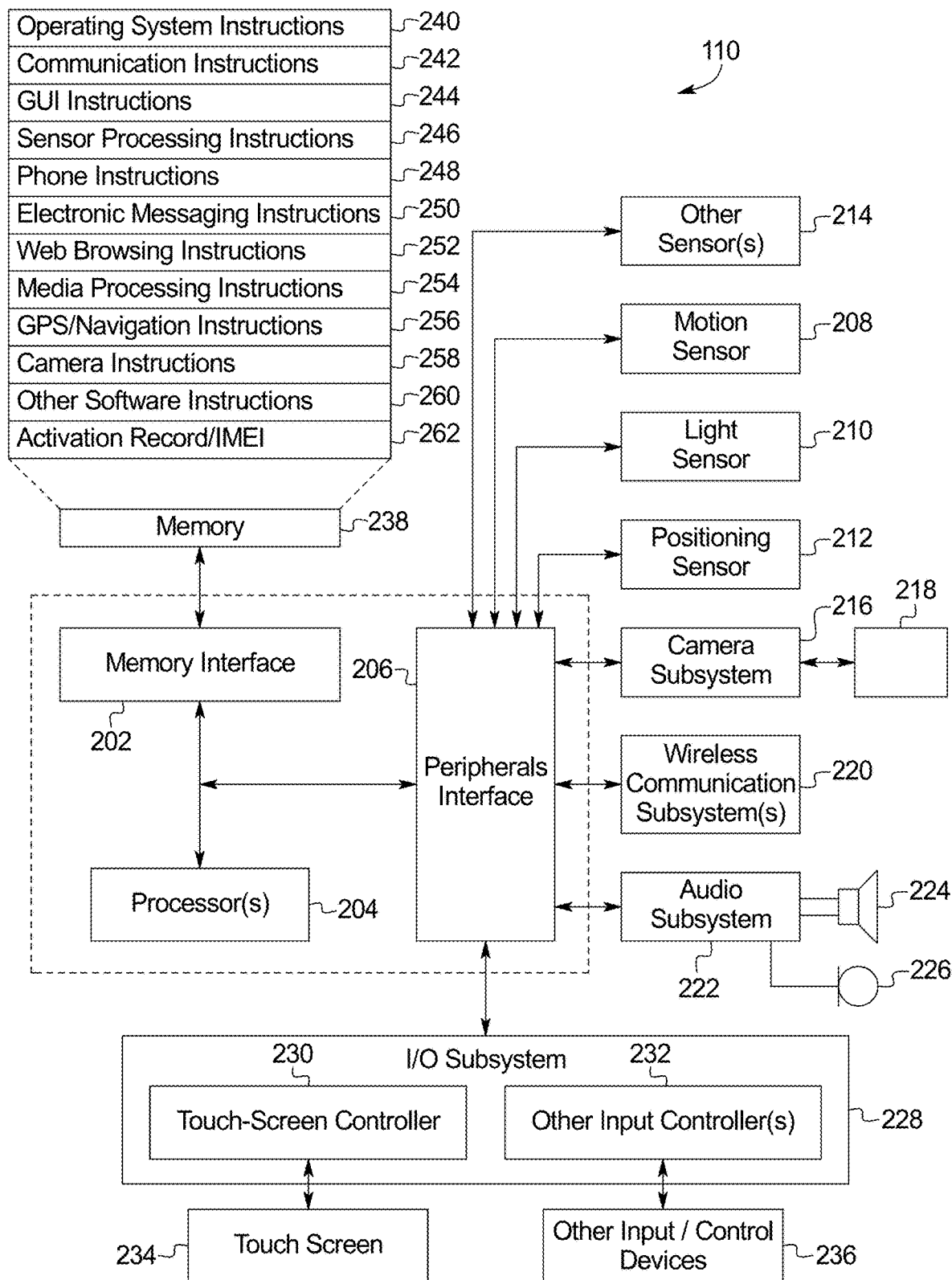
FIG. 9 is a schematic of an example of a user device for use in a system for generating a dietary plan including macronutrient mass value units.

FIG. 9 illustrates a schematic of an example of a user device 110, 150a, 150b, 150c for use in the system 100 for generating a dietary plan including macronutrient mass value units. As shown in FIG. 9, the user device 110 includes a memory interface 202, one or more data processors, image processors and/or central processors 204, and a peripherals interface 206. The memory interface 202, the one or more processors 204 and/or the peripherals interface 206 can be separate components or can be integrated in one or more integrated circuits. The various components in the user device 110 can be coupled by one or more communication buses or signal lines, as will be recognized by those skilled in the art.

Sensors, devices, and additional subsystems can be coupled to the peripherals interface 206 to facilitate various functionalities. Other sensors 214 can also be connected to the peripherals interface 206, such as a proximity sensor, a temperature sensor, a biometric sensor, or other sensing device, to facilitate related functionalities.

A camera subsystem 216 and an optical sensor 218 (e.g., a charged coupled device (CCD) or a complementary metal-oxide semiconductor (CMOS) optical sensor) can be utilized to facilitate camera functions, such as recording photographs and video clips.

Communication functions can be facilitated through one or more wireless communication subsystems 220, which can include radio frequency receivers and transmitters and/or optical (e.g., infrared) receivers and transmitters. The specific design and implementation of the communication subsystem 220 can depend on the communication network(s) over which the user device 110 is intended to operate. For example, the user device 110 can include communication subsystems 220 designed to operate over an LTE network, a GSM network, a GPRS network, an EDGE network, a Wi-Fi or WiMax network, and a Bluetooth™ network. In particular, the wireless communication subsystems 220 may include hosting protocols such that the user device 110 may be configured as a base station for other wireless devices.

An audio subsystem 222 can be coupled to a speaker 224 and a microphone 226 to facilitate voice-enabled functions, such as voice recognition, voice replication, digital recording, and telephony functions.

The I/O subsystem 228 can include a touch screen controller 230 and/or other input controller(s) 232. The touch-screen controller 230 can be coupled to a touch screen 234. The touch screen 234 and touch screen controller 230 can, for example, detect contact and movement, or break thereof, using any of a plurality of touch sensitivity technologies, including but not limited to capacitive, resistive, infrared, and surface acoustic wave technologies, as well as other proximity sensor arrays or other elements for determining one or more points of contact with the touch screen 234. The other input controller(s) 232 can be coupled to other input/control devices 236, such as one or more buttons, rocker switches, thumb-wheel, infrared port, USB port, and/or a pointer device such as a stylus. The one or more buttons (not shown) can include an up/down button for volume control of the speaker 224 and/or the microphone 226.

The memory interface 202 can be coupled to memory 238. The memory 238 can include high-speed random access memory and/or non-volatile memory, such as one or more magnetic disk storage devices, one or more optical storage devices, and/or flash memory (e.g., NAND, NOR). The memory 238 can store operating system instructions 240, such as Darwin, RTXC, LINUX, UNIX, OS X, iOS, WINDOWS, ANDROID or an embedded operating system such as VxWorks. The operating system instructions 240 may include instructions for handling basic system services and for performing hardware dependent tasks. In some implementations, the operating system instructions 240 can be a kernel (e.g., UNIX kernel).

The memory 238 may also store communication instructions 242 to facilitate communicating with one or more additional devices (e.g., the first user fitness tracker 120), one or more computers and/or one or more servers (e.g., the server 130). The memory 238 may include graphical user interface instructions 244 to facilitate graphic user interface processing; sensor processing instructions 246 to facilitate sensor-related processing and functions; phone instructions 248 to facilitate phone-related processes and functions; electronic messaging instructions 250 to facilitate electronic-messaging related processes and functions; web browsing instructions 252 to facilitate web browsing-related processes and functions; media processing instructions 254 to facilitate media processing-related processes and functions; GPS/Navigation instructions 256 to facilitate GPS and navigation-related processes and instructions; camera instructions 258 to facilitate camera-related processes and functions; and/or other software instructions 260 to facilitate other processes and functions (e.g., access control management functions, etc.). The memory 238 may also store other software instructions (not shown) controlling other processes and functions of the user device 110 as will be recognized by those skilled in the art. In some implementations, the media processing instructions 254 are divided into audio processing instructions and video processing instructions to facilitate audio processing-related processes and functions and video processing-related processes and functions, respectively. An activation record and International Mobile Equipment Identity (IMEI) 262 or similar hardware identifier can also be stored in memory 238.

Each of the above identified instructions and applications can correspond to a set of instructions for performing one or more functions described herein. These instructions need not be implemented as separate software programs, procedures, or modules. The memory 238 can include additional instructions or fewer instructions. Furthermore, various functions of the user device 110 may be implemented in hardware and/or in software, including in one or more signal processing and/or application specific integrated circuits.

In one example, the memory 238 includes stored instructions that, when executed by the processor 204, cause it to perform the features and functions related to the generation and communication of a dietary plan including macronutrient mass value units, as described herein.

It should be noted that various changes and modifications to the embodiments described herein will be apparent to those skilled in the art. Such changes and modifications may be made without departing from the spirit and scope of the present invention and without diminishing its attendant advantages. For example, various embodiments of the systems and methods may be provided based on various combinations of the features and functions from the subject matter provided herein.

I claim:

1. A system for generating a dietary plan including macronutrient mass value units, wherein the system comprises:
   a controller;
   a heart rate monitor in communication with the controller;
   a memory coupled to the controller, wherein the memory is configured to store program instructions executable by the controller;
   wherein in response to executing the program instructions, the controller is configured to:
   receive a goal weight value from a user;
   over a first period of time, receive weight data from a scale in communication with the controller;
   over the first period of time, receive dietary data and exercise data, wherein the exercise data is automatically uploaded from the heart rate monitor;
   determine a carbon dioxide mass loss over the first period of time based on the exercise data;
   determine a consumed insulin load over the first period of time based on the dietary data;
   generate at least two insulin load values based on the consumed insulin load over the first period of time, the carbon dioxide mass loss over the first period of time, the weight data over the first period of time, and the goal weight,
   wherein a first insulin load value is a maximum amount of a first insulin load the user can consume in order to achieve the goal weight in a first time length, wherein a second insulin load value is a maximum amount of a second insulin load the user can consume in order to achieve the goal weight in a second time length, wherein the first time length is greater than the second time length; and
   display the two generated insulin load values on the user interface, wherein the carbon dioxide mass loss ($m_{CO2}$) is determined using formula 1, $$m_{CO_2} = \dot{v}_{CO_2} \rho r^{-1} \qquad (1)$$

wherein $\rho$ is density of air, r=29 g mol$^{-1}$/44 g mol$^{-1}$, wherein $\dot{v}$ is calculated by formula (2), $$\dot{v} = a + b \ln(HR) \qquad (2)$$

wherein $\dot{v}$ is the volume of air in liters released by an individual in one minute and a and b are coefficients of the empirical fit based on age, gender, and fitness level, wherein HR is heart rate, wherein a and b are determined by monitoring heart rate as a function of time when the user is fasting based on a mass loss rate that is measured using an accurate scale.

2. The system of claim 1, wherein the controller is further configured to receive via a user interface user profile information, wherein the user profile information includes age, race, gender, weight, height, blood pressure, cholesterol, or combinations thereof, wherein the at least two insulin load values are based on user profile information.

3. The system of claim 1, wherein the dietary data is received from the user.

4. The system of claim 1, wherein the controller is further configured to determine at least one of glycemic index, glycemic score, glycemic load, insulin index, or insulin score based on the dietary data.

5. The system of claim 1, wherein the dietary data is received automatically from a food tracking system.

6. The system of claim 1, wherein the controller is further configured to modify the generated at least two insulin values based on the most recent input dietary data, exercise data, and weight data.

7. The system of claim 1, wherein the controller is further configured to generate a macronutrient value, based on the consumed insulin load, the carbon dioxide mass loss, weight data, and the goal weight, wherein the macronutrient value is a carbohydrate value, protein value, fat value, fiber value, sugar value, water value, glycemic index, glycemic score, glycemic load, insulin index, insulin score, or satiety index.

8. A system for generating a dietary plan including macronutrient mass value units, wherein the system comprises:
   a controller;
   a heart rate monitor in communication with the controller;
   a memory coupled to the controller, wherein the memory is configured to store program instructions executable by the controller;
   wherein in response to executing the program instructions, the controller is configured to:
   receive a goal weight value from a user;
   over a first period of time, receive weight data from a scale in communication with the controller;
   over the first period of time, receive dietary data and exercise data, wherein the exercise data is automatically uploaded from the heart rate monitor;
   determine a carbon dioxide mass loss over the first period of time based on the exercise data;
   determine a consumed insulin load over the first period of time based on the dietary data;
   generate at least two insulin load values based on the consumed insulin load over the first period of time, the carbon dioxide mass loss over the first period of time, the weight data over the first period of time, and the goal weight, wherein a first insulin load value is a maximum amount of a first insulin load the user can consume in order to achieve the goal weight in a first time length, wherein a second insulin load value is a maximum amount of a second insulin load the user can consume in order to achieve the goal weight in a second time length, wherein the first time length is greater than the second time length; and display the two generated insulin load values on the user interface wherein the carbon dioxide mass loss ($m_{CO_2}$) is determined using formula 1, $$m_{CO_2} = \dot{v}_{CO_2} \rho r^{-1} \quad (1)$$

wherein $\rho$ is density of air, $r = 29 \text{ g mol}^{-1}/44 \text{ g mol}^{-1}$, wherein $\dot{v}$ is calculated by formula (2), $$\dot{v} = a + b \ln(HR) \quad (2)$$

wherein $\dot{v}$ is the volume of air in liters released by an individual in one minute and a and b are coefficients of the empirical fit based on age, gender, and fitness level, wherein HR is heart rate, wherein a and b are determined by monitoring heart rate as a function of time when the user is fasting based on a mass loss rate that is measured using an accurate scale.

* * * * *